United States Patent [19]

Bates

[11] Patent Number: 4,650,472
[45] Date of Patent: Mar. 17, 1987

[54] APPARATUS AND METHOD FOR EFFECTING PERCUTANEOUS CATHETERIZATION OF A BLOOD VESSEL USING A SMALL GAUGE INTRODUCER NEEDLE

[75] Inventor: Brian L. Bates, Bloomington, Ind.

[73] Assignee: Cook, Incorporated, Bloomington, Ind.

[21] Appl. No.: 771,025

[22] Filed: Aug. 30, 1985

[51] Int. Cl.<sup>4</sup> ............................................. A61M 5/00
[52] U.S. Cl. .................... 604/158; 604/170; 604/165; 128/658
[58] Field of Search ............ 604/158, 161, 164, 170, 604/264, 280, 283; 128/656, 658

[56] References Cited

U.S. PATENT DOCUMENTS

| | | | |
|---|---|---|---|
| 3,903,885 | 9/1975 | Fuchs | 604/165 X |
| 4,230,123 | 10/1980 | Hawkins, Jr. | 128/658 |
| 4,239,042 | 12/1980 | Asai | 604/164 |
| 4,306,562 | 12/1981 | Osborne | 604/164 X |
| 4,405,314 | 9/1983 | Cope . | |
| 4,538,622 | 9/1985 | Sampson et al. | 604/170 X |

Primary Examiner—Stephen C. Pellegrino
Attorney, Agent, or Firm—Woodard, Weikart, Emhardt & Naughton

[57] ABSTRACT

A apparatus and method for percutaneous catheterization of a blood vessel permitting use of a small gauge needle is shown. A 22 gauge needle is used for making the initial entry into the blood vessel. A wire guide is then introduced into the blood vessel through the introducer needle, the needle then being withdrawn. A catheter and an inner cannula are passed in unison over the wire guide, through the skin and into the blood vessel. The cannula is provided with a tapered tip which extends through the distal opening of the catheter, thereby providing a diametrical transition between the small wire guide and the relatively larger catheter, resulting in a minimum of trauma during insertion. Once the catheter is in place, the inner cannula and wire guide are withdrawn, leaving the catheter in place with a relatively large distal opening, thereby promoting good fluid flow characteristics of the catheter.

5 Claims, 12 Drawing Figures

APPARATUS AND METHOD FOR EFFECTING PERCUTANEOUS CATHETERIZATION OF A BLOOD VESSEL USING A SMALL GAUGE INTRODUCER NEEDLE

BACKGROUND OF THE INVENTION

The present invention relates to the field of percutaneous catheterization of blood vessels.

Many medical procedures require the percutaneous placement of a catheter into a vein or artery. Catheterization of this type is used for blood pressure monitoring, blood sampling, or administration of drugs and fluids, for example. Until now, such catheters have usually been inserted by the technique described by Seldinger (Acta Radiologica. 39 [1953], 368–376). The Seldinger technique makes use of a relatively small gauge introduction needle which allows entry into a vessel without a cutdown and with minimal trauma to the vessel and surrounding tissue. More specifically, the vessel is entered obliquely by introducing a small thinwall percutaneous lancet beveled needle through the skin and into the blood vessel. A somewhat stiff, but flexible, wire guide is then inserted through the bore of the needle about 5 to 10 cm into the vessel. While holding the wire guide in place, the needle is withdrawn. The catheter, having a tapered tip, is then inserted by sliding it over the wire guide and, with a twisting motion, advancing it through the skin at the needle puncture site and into the vessel. Once the catheter is in place within the blood vessel, the wire guide is withdrawn.

Conventional wire guides as used in the above procedure are comprised of a tightly wound helical stainless steel wire coil. Such wire guides, to have sufficient rigidity to properly support and lead standard catheters, are typically constructed with a diameter of 0.035 inches (20 gauge). The smallest standard needle which will allow a 0.035 inch wire guide to pass through it is an 18 gauge needle (0.049 inch), and thus the 18 gauge needle has become the standard needle for use with the Seldinger Technique for percutaneous catheterization.

Because of the unavoidable tissue trauma that results from insertion of a lancet beveled needle, it is desirable that as small a needle as possible be used to effect the initial entry. The present invention involves an improved Seldinger technique which utilizes a novel catheterization apparatus which allows a smaller gauge needle, namely 22 gauge (0.028 inch dia.), to be used for percutaneous insertion of standard catheters and catheter introducing sheaths of up to at least French size 9 (0.118 inch dia.). For convenience, the word "catheter" will be used below to refer to both catheters and catheter introducing sheaths, as they are analogous structures with respect to the present invention.

The principles upon which the present invention is based can be described briefly, as follows. Wire guides in the range of 0.018 inches in diameter (26 gauge) are now available with sufficient stiffness to be used confidently for introducing a catheter in the French size 5 to 9 range. Wire guides of this type are available from Cook, Incorporated, 925 South Curry Pike, P.O. Box 489, Bloomington, Indiana 47402, sold as the Cor-Flex TM line of wire guides. To use such a small diameter wire guide with such relatively large catheters, it is necessary to provide the distal end of the catheter with a smooth diametrical transition from the wire guide to the full diameter of the catheter. This enables the catheter to be more easily inserted through the skin at the puncture site with a minimum of tissue trauma. One way of accomplishing this would be to provide the external diameter of the catheter with a long gradually tapered tip which narrows at its distal end to a diameter only slightly larger than the wire guide. Likewise, the internal lumen of the catheter would have an opening at the distal end with a diameter only slightly larger than the wire guide.

One disadvantage of the long tapered tip approach is that the distal opening would necessarily be very small, on the order of 0.018 inches, which would impair the performance of the catheter by restricting fluid flow therethrough. Furthermore, it is known that long tapers are not desirable once inside the vessel, since they are likely to erode or damage the vessel wall.

The above mentioned problems are overcome or alleviated by the present invention, one principle of which is the provision of a catheter having a removable cannula located over the wire guide but inside the catheter. The cannula has a tapered tip which extends through the distal opening of the catheter, providing a diametrical transition between the large distal opening of the catheter and the wire guide. The catheter and the cannula are inserted into the blood vessel in unison. Once the catheter is properly positioned within the blood vessel, the cannula can be withdrawn, leaving the catheter in place. Thus, a catheter can be inserted percutaneously into a blood vessel using a wire guide and introducer needle which are much smaller in diameter than the distal opening of the catheter. This ensures good flow characteristics for the catheter and a minimum of tissue trauma to the patient.

SUMMARY OF THE INVENTION

A catheterization set for percutaneous catheterization of a blood vessel, according to one aspect of the present invention, includes a hollow thin wall introducer needle having a lumen therethrough, wherein the introducer needle is about 22 gauge and has an outer diameter of about 0.028 inches. Also included is a wire guide sized to be received through the lumen of the introducer needle. A catheter smaller than about French size 9 having proximal and distal open ends and a lumen therethrough is another element of such a set. Further provided is a cannula having proximal and distal open ends and a lumen therethrough, the cannula sized to be received within the lumen of the catheter, the lumen of the cannula sized to receive the wire guide therethrough, and the distal opening being just large enough to receive the wire guide freely therethrough. The cannula has a tapered distal portion having an outer diameter decreasing toward the distal end and sized to extend through the distal opening of the catheter to provide a smooth diametrical transition between the distal end of the catheter and the distal opening of the cannula.

It is an object of the present invention to provide a catheterization set and method of catheterization which permits percutaneous catheterization of blood vessels using a very small gauge introducer needle, thereby minimizing tissue trauma during insertion of the catheter.

Further objects and advantages of the present invention will be apparent to those skilled in the art from the following description and the claims appended below.

BRIEF DESCRIPTION OF THE DRAWINGS

FIGS. 5a–5e show sequentially certain aspects of the preferred method of catheterization of the present invention, using the catheterization set of FIGS. 1–4a.

DESCRIPTION OF THE PREFERRED EMBODIMENT

Figure 1:
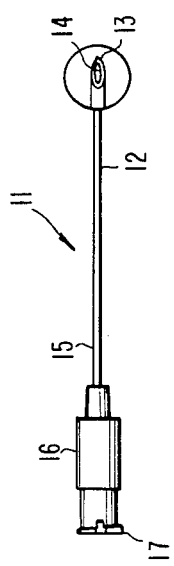
FIG. 1 is an elevational view of a small gauge introducer needle comprising a portion of a catheterization set made in accordance with the present invention.

For the purposes of promoting an understanding of the present invention, reference will now be made to the embodiments and method illustrated in the drawings and specific language will be used to describe the same. It is nevertheless to be understood that no limitation of the scope of the invention is thereby intended, the proper scope of the invention being indicated by the claims appended below and the equivalents thereof.

Referring to FIGS. 1–4a, there is illustrated the several components which in combination comprise one embodiment of a catheterization set made in accordance with the present invention. For clarity, some of the components are illustrated separately from one another while others are illustrated in their intended cooperative relationship. The figures are not all drawn to the same scale to avoid obscuring the details of the finer structures. The following detailed description of the embodiment will make clear the preferred arrangement, size relationships and method of use of the components shown herein.

Illustrated in FIG. 1 is a thin-wall hollow percutaneous introducer needle 11, including a standard 22 gauge (0.028 inch diameter) stainless steel cannula 12 having a lancet beveled tip 13 (shown enlarged) and a lumen 14 therethrough. Attached at end 15 of steel cannula 12 opposite tip 13 is a plastic hub 16 equipped with a standard Luer lock type connector 17. Hub 16 has a passageway therethrough in alignment with and communicating with lumen 14, the passageway being at least as great in diameter as lumen 14. In short, needle 11 is a conventional 22 gauge percutaneous needle of a selected length as is appropriate for the particular vessel which is to be catheterized.

Figure 2:
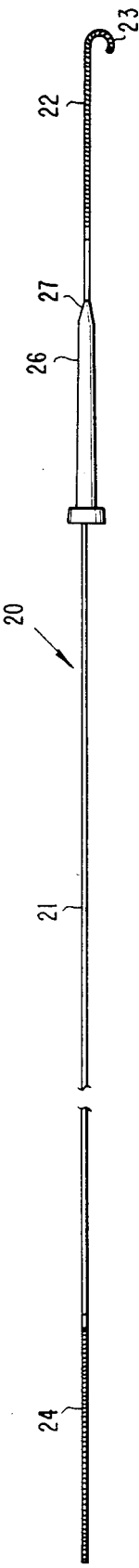
FIG. 2 is an elevational view of a small diameter solid mandrel wire guide and a wire guide straightener, both comprising further portions of a catheterization set made in accordance with the present invention.

Referring to FIG. 2, there is illustrated a wire guide 20 which is particularly suited for use in combination with the other components comprising the embodiment of the present invention. As shown, wire guide 20 includes a mandrel 21 which is made of solid stainless steel wire about 0.018 inches in diameter, which diameter enables wire guide 20 to pass through the bore of introducer needle 11. Soldered to opposite ends of mandrel 21 are flexible tips 22 and 24. Flexible tip 22 includes a preformed curved portion 23, while flexible tip 24 at the opposite end is straight. Each of the flexible tips 22 and 24 is comprised of stainless steel wire tightly wound in a helical coil. As a safety measure, a safety wire 25 (see FIG. 2a) is disposed longitudinally within the helical coil and soldered to each end of the coil portion. Thus, should the coil portion break while within a blood vessel, the safety wire will retain the broken portion attached to the wire guide so that it can be withdrawn from the body.

The construction of wire guide 20 in large part enables the advantageous combination of the components of the catheterization set, making it possible to accomplish the principle object of the present invention which is to minimize trauma by effecting percutaneous catheterization of a blood vessel using a small gauge introducer needle. In particular, by utilizing a wire guide with a solid mandrel rather than a full length helical coil, greater stiffness can be achieved at a smaller diameter than with conventionally constructed wire guides. At the same time, safety is enhanced by providing the tips of the wire guide with conventional helical coil construction to promote flexibility of the tips. While wire guide 20 is illustrated as having flexible tips at both ends, this is not strictly necessary as only one end is used for a particular catheterization. It will also be apparent to those skilled in the art that the flexible tips could be preformed in configurations other than straight or a simple curve, according to the demands of the particular procedure.

Referring again to FIG. 2, there is illustrated a wire guide straightener 26 disposed over wire guide 20. Wire guide straigtener 26 is essentially an elongated plastic member having a lumen therethrough sized just large enough to allow wire guide 20 to pass freely therethrough. By sliding wire guide straightener 26 along wire guide 20 until curved portion 23 is disposed wholly within the lumen thereof, the curved portion 23 of flexible tip 22 will be temporarily straightened. Then, with the tapered tip 27 engaging the hub 16 of introducer needle 11, the curved flexible tip 22 can be easily introduced into the lumen 14 of introducer needle 11 according to the method of the present invention.

Figure 2A:
FIGS. 2a and 2b are enlarged elevational views of the end portions of the wire guide of FIG. 2.
Figure 2B:
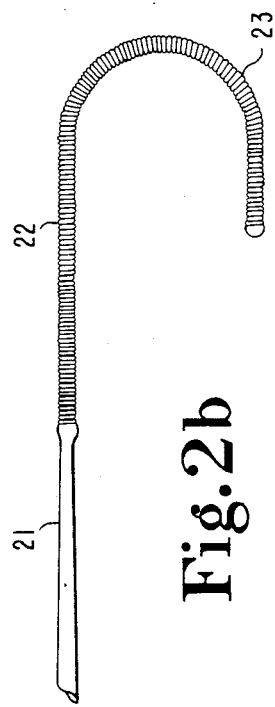

FIGS. 2a and 2b are enlarged views of flexible tips 22 and 24 which illustrate the attachment of the coil portions to the solid mandrel. In particular, it should be noted that the overall diameter of the flexible tips is no greater than the maximum diameter of the solid mandrel to which they are attached.

Figure 3:
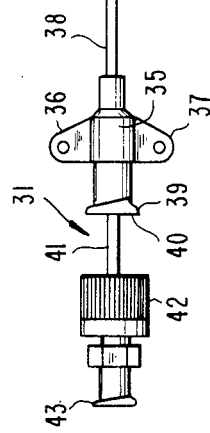
FIG. 3 is an elevational view of a catheter with a cannula therein comprising further portions of a catheterization set made in accordance with the present invention, and particularly showing the cannula partially inserted into the catheter.
Figure 4:
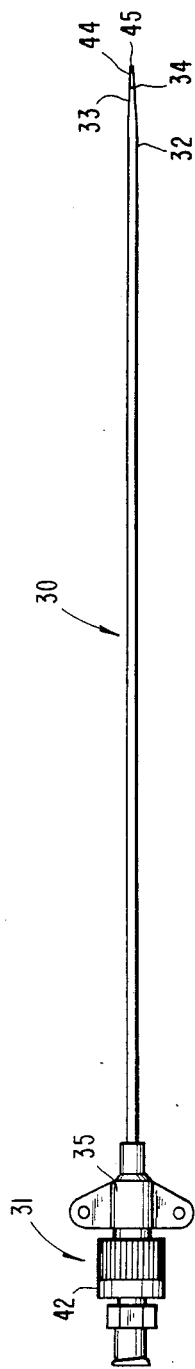
FIG. 4 is an elevational view of the catheter and cannula of FIG. 3, particularly showing the cannula fully inserted into the catheter.

Referring now to FIG. 3, there is illustrated two additional components of a catheterization set in accordance with the present invention, namely, catheter 30 and cannula 31. As shown, cannula 31 is disposed partially within catheter 30. During a particular point in the preferred method of use of the catheterization set, cannula 31 is disposed more fully within catheter 30, as illustrated in FIG. 4 and as discussed further below. Catheter 30 includes a plastic catheter tube 32 in the range of about French size 3 to 9 and having a lumen therethrough, catheter tube 32 preferably being composed of radiopaque polyethylene, although it alternately can be made of teflon and other plastics as are typically used in the catheter art. Catheter tube 32 is configured with a slight taper at the distal end 33 terminating at distal opening 34. Distal opening 34 is significantly larger in diameter than wire guide 20, with a diameter of about 0.039 inches being typical.

Continuing to refer to FIG. 3, catheter 30 further includes a hub 35 having a pair of radially protruding wings 36 and 37 fixed to proximal end 38 of catheter tube 32, and a standard Luer lock type connector 39. Wings 36 and 37 can be used as anchor points for securing the catheter in place after it has been inserted, such as by taping them to the patient's skin. Hub 35 has a passageway therethrough in alignment with and communicating with the lumen of catheter tube 32, the passageway being at least as great in diameter as the lumen. The passageway through hub 35 terminates in proximal opening 40.

Also shown in FIG. 3 is cannula 31, including cannula tube 41 which is sized to fit freely within the lumen of catheter tube 32. Cannula tube 41 is essentially a plastic tube having a lumen therethrough, the lumen of cannula tube 41 being sized to receive wire guide 20 freely therein. Attached to the proximal end of cannula tube 41 is connector hub 42 which terminates in a Luer lock connector 43. Connector hub 42 is configured to releasably engage and connect with Luer lock connector 39 to temporarily maintain catheter tube 32 and cannula tube 41 in fixed longitudinal relationship with respect to each other, as illustrated in FIG. 4. Connector hub 42 and Luer lock connector 43 have a passageway therethrough aligned with and communicating with the lumen of cannula tube 41. As illustrated in FIG. 3, cannula 31 is disconnected from and partially withdrawn from catheter 30.

Referring in particular to FIG. 4, cannula 31 is shown disposed fully within catheter 30. Connector hub 42 is in engagement with hub 35 and the distal tip 44 of cannula tube 41 extends through distal opening 34 of catheter tube 32. Cannula tube 41 terminates in distal opening 45 which is just slightly larger in diameter than wire guide 20, that is, it is just large enough to receive wire guide 20 freely therethrough.

Figure 4A:
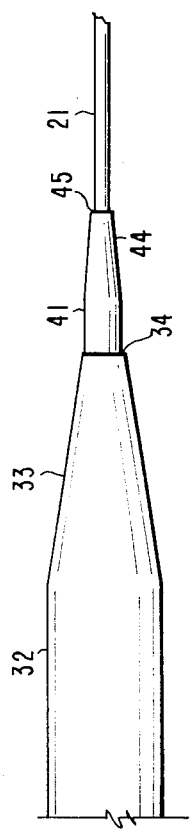
FIG. 4a is an enlarged elevational view of a portion of the catheter and cannula of FIG. 3 configured as shown in FIG. 4, and particularly showing the distal end portion.

FIG. 4a is an enlarged view of the distal end of catheter tube 32 showing the relationship of cannula tube 41 thereto when disposed as in FIG. 4. Wire guide 20 is also shown disposed within cannula tube 41 and extending through distal opening 45 to illustrate the diametrical relationship between the three components. As can be seen, the tapered distal tip 44 provides a diametrical transition from distal opening 34 of catheter tube 32 to distal opening 45 of cannula tube 41, thereby providing a smooth diametrical transition from wire guide 20 to the maximum diameter of catheter tube 32, when wire guide 20, cannula tube 41 and catheter tube 32 are disposed as shown.

Figure 5A:
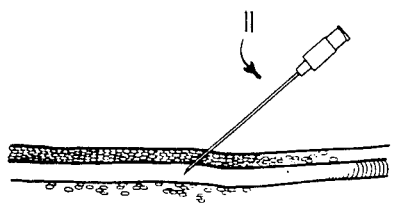
Figure 5B:
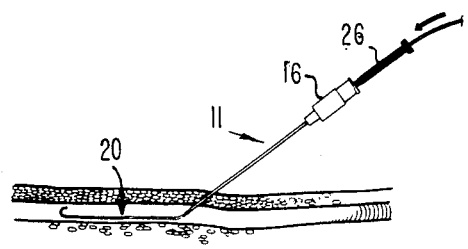
Figure 5C:
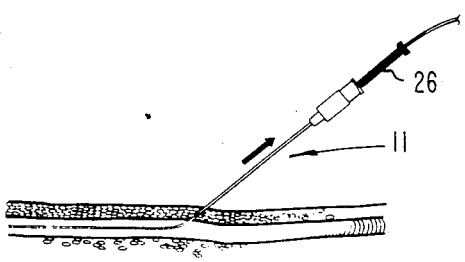
Figure 5D:
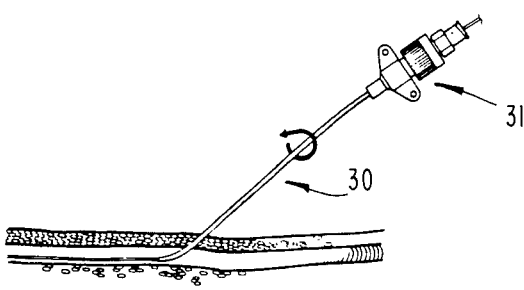
Figure 5E:
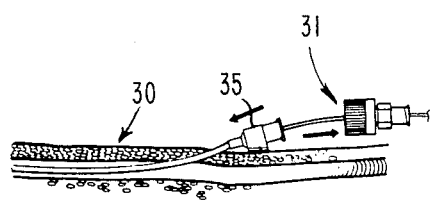

Referring now to FIGS. 5a through 5e, the preferred method of catheterization using the above described catheterization set is set forth briefly. As shown in FIG. 5a, the first step involves introducing the thin-wall percutaneous introducer needle 11 into the vessel. Second, as shown in FIG. 5b, wire guide straightener 26 is slid over the curved portion of wire guide 20 and then the tip of the wire guide straightener is inserted into the needl hub 16. Temporarily straightened wire guide 20 is passed through the needle and advanced about 5-10 cm into the vessel. Looking now at FIG. 5c, the needle and wire guide straightener are withdrawn, leaving the wire guide in place. As shown in FIG. 5d, the catheter 30 and inner cannula 31 are passed over the wire guide in unison and advanced with a twisting motion into the blood vessel. FIG. 5e shows the wire guide and inner cannula being removed, leaving the catheter 30 in place in the blood vessel.

While the preferred embodiments and method of use of the invention have been illustrated and described in some detail in the drawings and foregoing description, it is to be understood that this description is made only by way of example to set forth the best mode contemplated of carrying out the invention and not as a limitation to the scope of the invention which is pointed out in the claims below.

What is claimed is:

1. A catheterization set for percutaneous catheterization of a blood vessel, comprising:
   a hollow thin wall introducer needle having a lumen therethrough, said introducer needle being about 22 gauge and having an outer diameter of about 0.028 inches;
   a wire guide sized to be received through the lumen of said introducer needle;
   a catheter smaller than about French size 9 having proximal and distal open ends and a lumen therethrough;
   a cannula having proximal and distal open ends and a lumen therethrough, said cannula sized to be received within the lumen of said catheter, the lumen of said cannula sized to receive said wire guide therethrough, the distal opening being just large enough to receive said wire guide freely therethrough, said cannula having a tapered distal portion having an outer diameter decreasing toward the distal end and sized to extend through the distal opening of said catheter to provide a smooth diametrical transition between the distal end of the catheter and the distal opening of said cannula; and
   means connected to the proximal ends of said catheter and said cannula for temporarily fixing the longitudinal disposition of each with respect to the other such that said catheter and cannula are a unitary structure with a smooth tapered distal end, said means for fixing including a first connector fixed to the proximal end of said cannula, the first connector having an opening therethrough aligned with and communicating with the lumen of said cannula, and a second connector fixed to the proximal end of said catheter tube, the second connector having an opening therethrough aligned with and communicating with the lumen of said catheter tube, the second connector being cooperatively connectable to the first connector to temporarily maintain the catheter tube and the inner cannula in fixed longitudinal relationship with respect to each other.

2. The catheterization set of claim 1, wherein said wire guide has a solid mandrel and a flexible tip, the flexible tip including a helically wound wire coil.

3. The catheter apparatus of claim 2, wherein said wire guide has a diameter of about 0.018 inches.

4. The catheterization set of claim 1, wherein said introducer needle has an outer diameter less than about 0.049 inches, said wire guide has a diameter less than about 0.035 inches, and said catheter tube is sized in the range of about French size 3 to about French size 9.

5. A method of percutaneous catheterization of a blood vessel, comprising the steps of:
   (a) providing a thin wall hollow percutaneous introducer needle having an outer diameter less than about 0.049 inches;

(b) providing a wire guide having a diameter less than about 0.035 inches and such that said wire guide is capable of passing through the bore of said introducer needle;

(c) providing an inner cannula having an open proximal end and an open distal end and a lumen therethrough communicating the distal end with the proximal end, said lumen having a diameter capable of receiving said wire guide therethrough, the distal opening of said inner cannula having a diameter slightly larger than said wire guide, said inner cannula having a smoothly taperd outer diameter at the distal end providing a decreasing diametrical transition to the distal end of said inner cannula, said inner cannula having a first connector fixed to the proximal end of said inner cannula, the first connector having an opening therethrough aligned with and communicating with the lumen of said cannula; and (d) providing a catheter tube sized in the range of about French size 3 to about French size 9, and having an open proximal end and an open distal end and a lumen therethrough communicating the proximal end with the distal end, said lumen having a diameter capable of receiving said inner cannula therethrough, the distal opening of said catheter tube having a diameter slightly larger than said inner cannula, said catheter tube having a second connector fixed to the proximal end of said catheter tube, the second connector having an opening therethrough aligned with and communicating with the lumen of said catheter tube, the second connector being cooperatively connectable to the first connector to temporarily maintain the catheter tube and the inner cannula in fixed longitudinal relationship with respect to each other;

(e) introducing said introducer needle into said blood vessel percutaneously;

(f) while maintaining said introducer needle in place within said blood vessel, guiding said wire guide through said needle and into said blood vessel;

(g) while maintaining said wire guide in place within said blood vessel, withdrawing said introducer needle;

(h) disposing said inner cannula within the lumen of said catheter tube with the tapered distal end of the inner cannula extending beyond the distal end of the catheter tube to provide a diametrical transition from the distal end of said catheter tube to the distal end of said inner cannula, and maintaining said inner cannula and said catheter tube in such relative disposition by connecting the second connector to the first connector;

(i) passing said inner cannula and said catheter tube in unison over said wire guide, and introducing said inner cannula/catheter tube into said blood vessel;

(j) while maintaining said inner cannula/catheter tube within said blood vessel, withdrawing said wire guide; and (k) while maintaining said catheter tube within said blood vessel, disconnecting the second connector from the first connector and withdrawing said inner cannula.

* * * * *